United States Patent [19]

Ikekawa

[11] Patent Number: 4,832,875
[45] Date of Patent: May 23, 1989

[54] VITAMIN $D_3$ DERIVATIVE

[75] Inventor: Nobuo Ikekawa, Musashino, Japan

[73] Assignee: Taisho Pharmaceutical Co., Ltd., Tokyo, Japan

[21] Appl. No.: 80,512

[22] PCT Filed: Nov. 21, 1986

[86] PCT No.: PCT/JP86/00598

§ 371 Date: Jul. 8, 1987

§ 102(e) Date: Jul. 8, 1987

[87] PCT Pub. No.: WO87/03282

PCT Pub. Date: Jun. 4, 1987

[30] Foreign Application Priority Data

Nov. 21, 1985 [JP] Japan .................................. 60-261810

[51] Int. Cl.⁴ ................................................ C07J 9/00

[52] U.S. Cl. ...................................................... 260/397.2
[58] Field of Search ....................................... 260/397.2

[56] References Cited

U.S. PATENT DOCUMENTS 4,226,788 10/1980 DeLuca et al. ................. 260/397.2
4,552,698 11/1985 DeLuca et al. ................. 260/397.2

*Primary Examiner*—Douglas W. Robinson
*Assistant Examiner*—Joseph A. Lipovsky
*Attorney, Agent, or Firm*—Wenderoth, Lind & Ponack

[57] ABSTRACT

This invention provides 1α,25-dihydroxy-24a,24a-difluoro-24-homovitamin $D_3$ and a process for its production. This compound has strong vitamin D activity and low toxicity and is useful for preventing and treating calcium pathobolism, osteoporosis, etc.

1 Claim, No Drawings

VITAMIN D₃ DERIVATIVE

TECHNOLOGICAL FIELD

This invention relates to a novel vitamin $D_3$ derivative, and more specifically, to 1α,25-dihydroxy-24a,24a-difluoro-24-homovitamin $D_3$ (1α,25-dihydroxy-24a,24a-difluoro-24-homocholecalciferol) and a process for its production.

Active-form vitamins D are drugs useful for preventing and improving bone symptoms in renal failure, reduced function of the parathyroid gland and osteoporosis. Furthermore, the activities of vitamin D homologs as an anticancer agent or a cancer eliminating agent have recently attracted attention. Much research has therefore been undertaken on their synthesis.

The vitamin D derivatives proposed heretofore, however, have not proved to be entirely satisfactory in regard to efficacy and toxicity, and it has been desired to develop vitamin D derivatives having higher pharmacological efficacy and lower toxicity.

Physiological functions well known as the mechanism of calcium metabolizing action of vitamin D include (1) absorption of calcium in the small intestines, (2) dissolution of calcium and inorganic phosphorus from bones, and (3) deposition of calcium on bones. When vitamin D is considered from the viewpoint of a therapeutic agent for diseases induced by bone calcium disorders such as osteoporosis and rachitis, the greatest problem is a side-effect such as calcification of tissues other than bones owing to a rise in blood calcium level.

Accordingly, an ideal vitamin D derivative would be one which has a weak action of dissolving calcium and inorganic phosphorus from the bones as compared with its action of absorbing calcium from the small intestines, or inhibits such dissolving action, and has a strong action of depositing calcium on the bones.

In spite of the recent research and development of many vitamin D derivatives, an ideal vitamin D derivative has not yet been developed. This means that in drug design, it is very difficult to separate the action of absorbing calcium from the small intestines, the action of dissolving calcium and inorganic phosphorus from bones and the action of depositing calcium on bones.

It has been made clear that many vitamin D derivatives so far synthesized all show actions of dissolving calcium from the bones, and these actions are stronger as the action of absorbing calcium from the small intestines is stronger. See, for example, Tateo Suda, Eiji Ozawa, and Eimei Takahashi: "Science of Bones" pages 176–177 (1985), Ishiyaku Shuppan, Tokyo; Raisz, L. G., Trummel, C. L., Holick, M. F. and DeLuca, H. F.: Science, 175, 768 (1972); C. Kaneko, S. Yamada, A. Sugimoto, T. Suda, M. Suzuki, C. Kakuta and S. Sasaki; Steroids, 23, 75 (1974); M. F. Holick, M. Garakedian, H. F. DeLuca: Science, 176, 1146 (1972); and N. Ikegawa, Biochemistry, 55, 1297 (1983).

The present inventor has conducted extensive work in search of a very ideal vitamin D derivative which has strong vitamin D activity and inhibits dissolution of calcium from bones. Unexpectedly, the inventor has found that by introducing fluorine atoms into the carbon skeleton at the 24a-positions of 24-homovitamin $D_3$, a vitamin D homolog can be obtained which in spite of having strong vitamin D activity, shows an action of inhibiting dissolution of calcium from bones and has low toxicity. This discovery has led to the accomplishment of the present invention.

DISCLOSURE OF THE INVENTION

According to this invention, 24a,24a-difluoro-1α,25-dihydroxy-24-homovitamin $D_3$ represented by the following formula

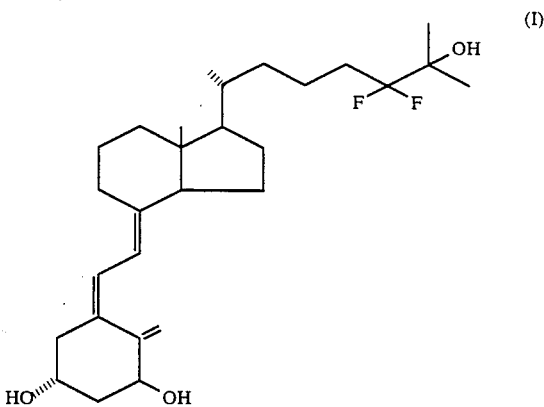

is provided as a novel compound.

According to this invention, the compound of formula (I) can be produced by the route shown by the following reaction scheme. In the following scheme, Ac represents an acyl group such as acetyl, and R represents a lower alkyl group such as methyl.

Reaction Scheme

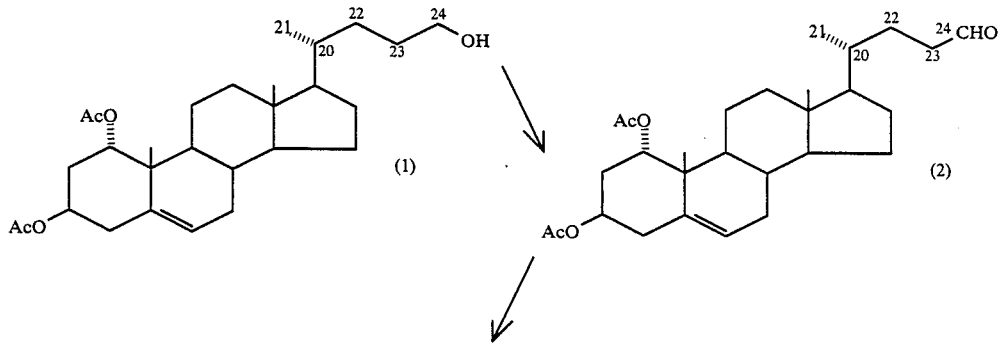

-continued
Reaction Scheme

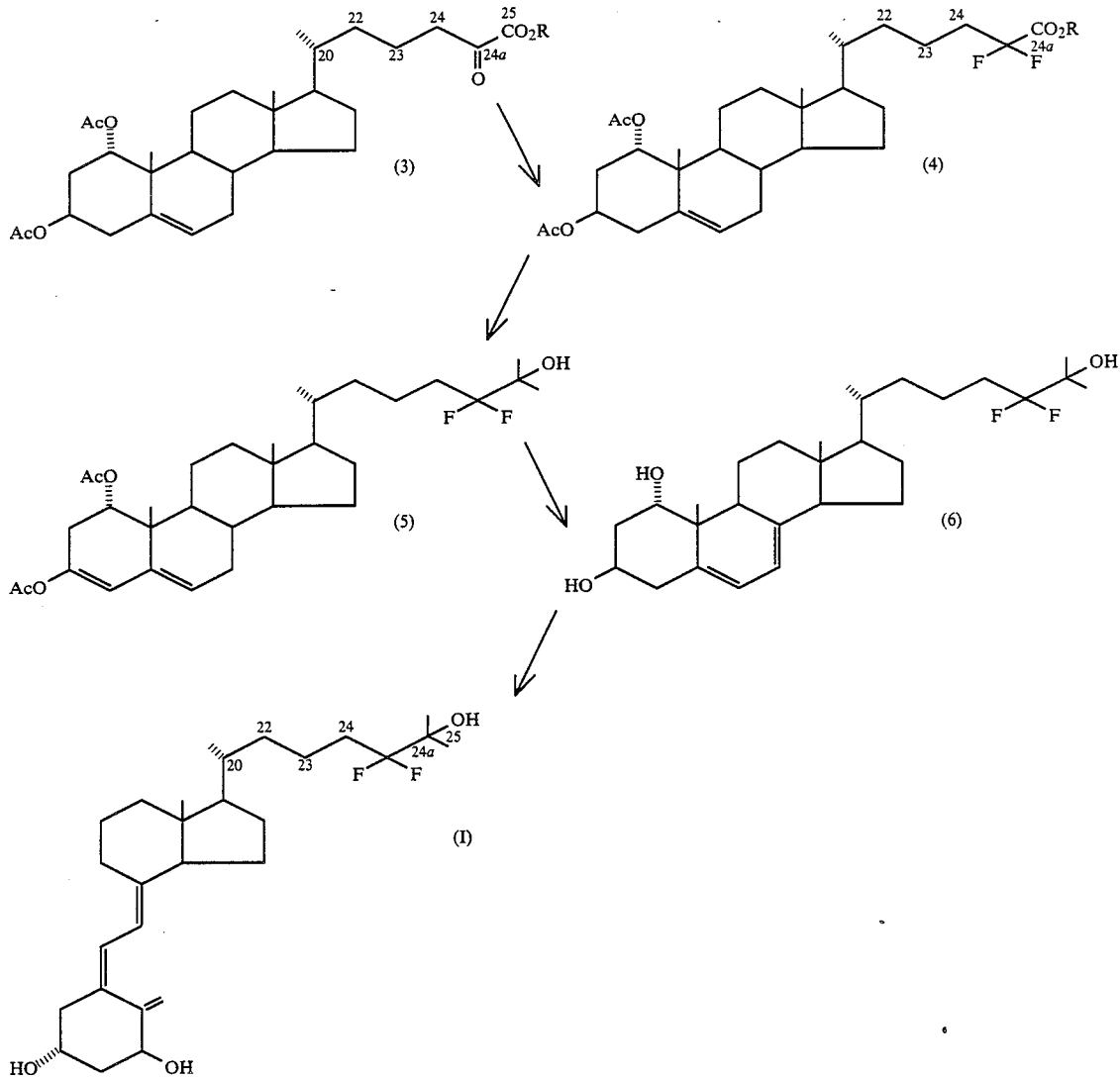

First, 1α,3β-diacetoxychol-5-en-24-ol represented by formula (1) is oxidized by the method of Swern et al. [J. Org. Chem., vol. 43, p. 2480 (1975)] to form the corresponding 24-aldehyde represented by formula (2). It is then treated with an anion prepared from a phosphonoacetate derivative represented by the following formula

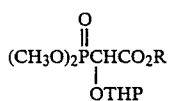 (7)

wherein R represents a lower alkyl group such as methyl, and THP represents a tetrahydropyranyl group, and n-butyllithium, to form an enol ether. Treatment of the enol ether with an acid to remove the tetrahydropyranyl group gives a carboxylate of formula (3). Preparation of the anion can be effected, for example, by reacting n-butyllithium with a nearly equimolar amount of the phosphonoacetate derivative of formula (7) in a suitable inert solvent (such as tetrahydrofuran), preferably in an inert gaseous atmosphere, and optionally in the presence of an organic base such as diisopropylamine. The reaction temperature used at this time is generally as low as about −80° C. to about −70° C. The anion so prepared can be immediately reacted with the 24-aldehyde of formula (2) at room temperature without isolation. This reaction gives the corresponding enol ether. By subsequently treating the enol ether with an acid such as p-toluenesulfonic acid in a solvent, the tetrahydropyranyl group can be removed. As a result, the carboxylate represented by formula (3) can be obtained.

The carboxylate of formula (3) so obtained is then reacted with diethylaminosulfur trifluoride at low temperatures in a solvent such as dichloromethane in an inert gaseous atmosphere. This gives a 24a,24a-difluoro ester represented by formula (4). This ester can be converted to a 25-alcohol compound represented by formula (5) by subjecting it to a Grignard reaction known per se using, for example, methylmagnesium bromide.

A double bond is introduced between the carbons at the 7- and 8-positions of the 25-alcohol compound, and the acyl groups at the 1α- and 3α-positions are removed, by, for example, hydrolysis to give a 1α,3α,25- trihydroxy-5,7-diene compound represented by formula (6). Introduction of the double bond can be carried out, for example, by brominating the carbon atom at the allylic position (7-position) with an equimolar or a slightly excessive molar amount of N-bromosuccinimide under heat, and then debrominating it using, for example, a tetra-n-butyl ammonium halide. Hydrolysis of the acyl groups may be carried out, for example by using an alcoholic solution of potassium hydroxide or sodium hydroxide.

Irradiation of ultraviolet light on the resulting compound of formula (6) gives the desired compound of formula (I). Ultraviolet irradiation on the compound of formula (6) can be carried out by dissolving the compound of formula (6) in a suitable solvent, for example, a hydrocarbon solvent such as hexane, octane or benzene, an ether solvent such as diethyl ether or tetrahydrofuran, an alcohol such as methanol or ethanol, preferably a lower alkanol, or a mixture thereof, preferably a low-boiling solvent, and exposing the resulting solution to ultraviolet irradiation. The effective wavelength of the ultraviolet light to be irradiated is in the range of 200 to 360 mn. Light beams from any light sources can be used if they include ultraviolet light having a wavelength in the above-specified range. Suitable irradiating light sources include, for example, a medium-pressure mercury lamp, a low-pressure mercury lamp, a high-pressure mercury lamp, and laser. As required, unwanted light beams may be cut off by using a filter.

The ultraviolet irradiation time varies depending upon the intensity of the light-source lamp or the scale of the reaction, but can generally be selected from the range of several tens of seconds to several hours.

The irradiation is carried out at a temperature in the range of usually about $-20°$ C. to about $120°$ C., preferably about $-10°$ C. to about $30°$ C., preferably in an inert gaseous atmosphere.

After the irradiation, the solution is heated in an inert gaseous atmosphere at a temperature between nearly room temperature to the refluxing temperature of the solvent, preferably at the refluxing temperature, for 1 to 2 hours to give the compound of formula (I).

The product may be isolated from the reaction mixture and purified by methods known per se, such as chromatography, extraction or recrystallization.

The $1\alpha,25$-dihydroxy-24a,24a-difluoro-24-homovitamin $D_3$ provided by the present invention has very high vitamin $D_3$ activity and an excellent action of enhancing calcium absorption and retention in vivo with reduced toxicity. Hence, the compound of formula (I) provided by this invention is useful as a drug for preventing and treating various diseases induced by abnormality and disorder of calcium balance and/or calcium absorption, such as calcium pathobolism and osteoporosis.

The following tests in vitro and in vivo demonstrate the excellent pharmacological activity of the compound of this invention.

TEST EXAMPLE 1

Test on receptor binding ability (in vitro)

Method 1,25-Dihydroxyvitamin $D_3$ receptor (Yamasa) prepared from the intestines of chicken embryo was suspended in TED buffer (10 mM Tris-HCl, 0.5 mM EDTA, 1 mM dithiothreitol; 10 mM Na , pH 7.4), and the resulting suspension is used as a receptor solution (protein about 0.5 mg/ml).

To the receptor solution was added 3 microliters or 10 microliters of an assay compound dissolved in 50% ethanol so as to provide a concentration of $10^{-9}$–$10^{-5}$M. Then, $1\alpha,25$-dihydroxyvitamin $D_3$ (about 0.4 mM) was added. The mixture was incubated at $0°$ C. for 3 hours.

The free assay compound and the assay compound bound to the receptor were separated by the charcoal method. The specific binding amount is obtained by subtracting the non-specific binding amount obtained in the presence of 10 $\mu$M of $1\alpha,25$-dihydroxyvitamin $D_3$ from the total binding amount obtained by the above reaction.

Results

TABLE 1

| Assay compound | Ability to bind to 1,25-dihydroxy-vitamin $D_3$ receptor in the intestines of chicken embryo Binding ability ($IC_{50}$*) |
| --- | --- |
| Compound of the invention | $5 \times 10^{-8}$ M |
| 1,25-Dihydroxy vitamin $D_3$ | $6.8 \times 10^{-8}$ M |

*50% inhibitory effect of 1,25-dihydroxy vitamin $D_3$ receptor binding

As shown in Table 1, the receptor binding ability of compound of this invention to 1,25-dihydroxyvitamin $D_3$ is recognized and its $IC_{50}$ value is $5.0 \times 10^{-8}$M.

Since the $IC_{50}$ value of 1,25-dihydroxyvitamin $D_3$ used as a control is $6.8 \times 10^{-8}$ the receptor binding ability of the compound of this invention is considered to be 1.36 times as strong as that of 1,25-dihydroxyvitamin $D_3$.

TEST EXAMPLE 2

The strong vitamin D receptor binding ability of the compound of this invention is considered to have basically to do with its possession of strong vitamin D activity. To confirm it in an in vivo (animal) test, however, its action of increasing the blood calcium level in vitamin D-deficient rats was examined.

Method

Wistar rats (male, three weeks old) purchased from Japan Charles River Co. were fed 3 to 4 weeks with a vitamin D-deficient diet containing calcium (0.02%) and phosphorus (0.99%) to prepare vitamin D-deficient rats. The compound of this invention or 1,25-dihydroxy-26,27-dimethylvitamin $D_3$ was orally administered to these animals once a day over 3 days. On the fourth day, blood was drawn from the animals, and calcium in the serum was measured by atomic absorptiometry.

As soon as the administration began, the feed was changed to one which was vitamin D-deficient but contained calcium in a normal amount (0.56%).

Results

TABLE 2

Activity of increasing calcium level in serum in vitamin D-deficient rats (the oral administration test conducted three times)

| Assay compound | Dosage (P moles/ rat, po) | Calcium in the serum (mg/dl) | Percent increase in serum Ca level (control 100%) |
| --- | --- | --- | --- |
| Control | — | 8.60 | 100 |

TABLE 2-continued

Activity of increasing calcium level in serum in vitamin D-deficient rats (the oral administration test conducted three times)

| Assay compound | Dosage (P moles/ rat, po) | Calcium in the serum (mg/dl) | Percent increase in serum Ca level (control 100%) |
|---|---|---|---|
| (ethanol) | | | |
| Compound of the invention | 600 | 9.80 | 114 |
| | 1,200 | 10.20 | 119 |
| 1,25-Dihydroxy-26,27-dimethyl-vitamin $D_3$ | 600 | 9.00 | 105 |
| | 1,200 | 9.60 | 112 |

As shown in Table 2, the compound of this invention shows an action of increasing the calcium level in the serum in animals being vitamin D-deficient but having normal calcium level. On the other hand, the 1,25-dihydroxy-26,27-dimethylvitamin $D_3$ as a control has a stronger action of increasing the calcium level in the serum than 1α-hydroxyvitamin $D_3$ or 1,25-dihydroxyvitamin $D_3$ as shown in Japanese Laid-Open Patent Publication No. 44860/1986.

Accordingly, the activity of the compound of this invention to increase the calcium level in the serum is considered to be stronger than that of 1,25-dihydroxyvitamin $D_3$. Thus, the effect of the in vitro test shown in Test Example 1 was also substantiated by the animal experiment.

TEST EXAMPLE 3

Test on the effect of inhibiting dissolution of calcium from bones

Vitamin D has both an action of calcium deposition on bones and an action of liberating calcium from the bones, and promotes bone formation when the balance between these actions is shifted toward the former. Accordingly, a vitamin D derivative which inhibits dissolution of calcium from bones can be expected to have a very strong bone-forming action. In the present test, calcium in the feed was limited to a low level, and under conditions in which no calcium absorption from the intestinal tract occurred, the activity to increase the calcium level in the serum was examined. This activity is considered to reflect calcium dissolution from the bones.

Method

The following test was conducted in accordance with the method of C. Kaneko et al. [C. Kaneko, S. Yamada, A. Sugimoto, M. Katuta, and S. Sasaki: Steroids, 23, 75 (1974)].

Three week old Wistar rats (male) were purchased from Japan Charles River Co., and were fed for 19 days with a feed being deficient in vitamin D and containing low calcium (0.02%) to prepare vitamin D-deficient hypocalcemia rats. An ethanol solution of an assay compound was intravenously administered once to the rats. On the next day, blood was drawn from the animals, and the calcium level in the serum was measured by atomic absorptiometry (using a double beam atomic absorption photometer made by Shimazu Seisakusho; Model AA-650).

Results

TABLE 3

Effect on the calcium level in the serum in vitamin D-deficient low-calcium rats (one intravenous administration)

| Assay compound | Dosage (P moles/ 100 g body weight) | Calcium in the serum (mg/dl) | Percent increase in serum Ca level (control 100%) |
|---|---|---|---|
| Control (ethanol) | — | 4.47 | 100 |
| Compound of the invention | 500 | 4.21* | 94.2 |

*There is a statistically significant difference at $P < 0.05$ with respect to the control.

For use as a medicament for the prevention and/or treatment of diseases such as calcium pathobolism and osteoporosis, the compound of this invention may be administered to mammals in a dose of about 25 to about 400 ng/day, preferably about 50 to about 200 ng/day. This dose range, however, is a provisional criterion, and the compound may be administered in doses outside this range in accordance with a physician's judgement depending upon the condition, sex, age and weight, for example, of the patient. The administration may be effected orally or parenterally through various routes (e.g., subcutaneous, intramuscular, intravenous, intraperitoneal, and intrarectal).

The compound of this invention may be formulated into a dosage form according to the route of administration. For example, for oral administration, it can be formulated into tablets, capsules, granules, powders, syrups, elixirs, etc. For parenteral administration, it can be formulated into injectable preparations, drops, suppositories, etc. A pharmaceutical composition in such dosage forms may be prepared by mixing an effective amount of the compound of this invention with a pharmaceutically acceptable carrier or diluent (adjuvant) and formulating the mixture into the desired dosage form in a usual manner.

Illustrative of the adjuvant which may be incorporated in solid preparations such as tablets, capsules, granules and powders are binders such as corn starch or gelatin; excipients such as dicalcium phosphate; disintegrants such as potato starch and alginic acid; lubricants such as magnesium stearate; sweetening agents such as sucrose; and flavors such as peppermint. Various other materials may be present as coatings or in order to otherwise modify the physical form of the dosage unit. For example, tablets may be coated with shellac, sugar, or both. The syrups or elixirs may contain the active compound, sucrose as a sweetening agent, methyl and propyl parabens as preservatives, a dye, and a flavor such as an orange flavor. Sterile compositions for injection can be formulated according to the conventional practice of pharmaceutical preparation by dissolving or suspending a fluorinated compound in a vehicle such as water for injection, a natural vegetable oil such as sesame oil, or a synthetic fatty acid vehicle such as ethyl oleate. Buffers, antiseptics and antioxidants may also be incorporated.

The following Example illustrates the present invention more specifically.

EXAMPLE

(a) Synthesis of 1α,3β-diacetoxychol-5-en-24-al (2)

Dimethyl sulfoxide (0.27 ml; 3.81 mmol) was added at −78° C. in an argon atmosphere to 5 ml of a dichloromethane solution of 0.17 ml (1.95 mmol) of oxalyl chloride, and the mixture was stirred for 10 minutes under the same conditions. To the resulting solution was added 3 ml of a dichloromethane solution o 432 mg (0.94 mmol) of 1α,3β-diacetoxychol-5-en-24-ol (1), and the mixture was further stirred for 15 minutes. Triethylamine (1.05 ml; 7.55 mmol) was added to the reaction mixture, and the mixture was stirred for 5 minutes. The temperature of the reaction mixture was returned to ambient temperature. It was treated in a customary manner (extracted with ether). The crude product was purified by silica gel column chromatography [30 g; eluted with hexane/ethyl acetate (5:1)] to give 382 mg of the captioned aldehyde (2).

$^1$H=NMR δ(ppm):
0.65 (3H, s), 1.04 (3H, s), 1.94 (3H, s),
1.97 (3H, s), 4.82 (1H, m), 4.98 (1H, m),
5.41 (1H, m), 9.58 (1H, t, J=1, 6Hz).

(b) Synthesis of methyl 1α,3β-diacetoxy-24a-oxo-24-homochol-5-ene-25-carboxylate (3)

In an argon atmosphere, 1.2 ml (2.04 mmol) of an n-butyllithium solution was added at −78° C. to 3 ml of a tetrahydrofuran (to be referred to as THF) solution of 0.3 ml (2.14 mmol) of diisopropylamine, and the mixture was stirred for 30 minutes. To the mixture was added 5 ml of a THF solution of 576 mg (2.04 mmol) of phosphonoacetate (7) (R=CH$_3$), and the mixture was stirred at −78° C. for 30 minutes. Then, 6 ml of a THF solution of 750 mg (1.64 mmol) of 1α,3β-diacetoxychol-5-en-24-al (2) obtained in (a) above was added, and the mixture was stirred at room temperature for 4 hours. The crude enol ether obtained by a conventional treatment (extraction with ether) was dissolved in a mixed solvent of 8 ml of THF and 5 ml of methanol, and 20 mg of p-toluenesulfonic acid was added. The mixture was stirred at room temperature for 40 minutes and then treated in a customary manner (extracted with ether). The resulting crude product was purified by silica gel column chromatography [22 g; eluted with hexane/ethyl acetate (5:1)] to give 530 mg of the captioned α-keto ester (3).

$^1$H=NMR δ(ppm):
0.65 (3H, s), 1.04 (3H, s), 1.94 (3H, s),
1.97 (3H, s), 2.74 (2H, t, J=6, 6Hz),
3.79 (3H, s), 4.85 (1H, m), 5.41 (1H, m).
EI-MS (30eV) m/z:
410 (M$^+$, 48.4%), 395 (6.5), 351 (3.6),
308 (4.2), 291 (7.3), 253 (3.9), 211 (6.5),
157 (8.4), 135 (15.8), 118 (base peak).

(c) Synthesis of methyl 1α,3β-diacetoxy-24a,24a-difluoro-24-homochol-5-ene-25-carboxylate (4)

Diethylaminosulfur trifluoride (0.6 ml; 4.93 mmol) was added at 0° C. in an argon atmosphere to 15 ml of a dichloromethane solution of 530 mg (1.00 mmol) of the methyl 1α,3β-diacetoxy-24a-oxo-24-homochol-5-ene-25-carboxylate (3), and the mixture was stirred at room temperature for 16 hours. The reaction mixture was treated in a customary manner (extracted with ethyl acetate). The resulting crude product was purified by silica gel column chromatography [38 g; eluted with hexane/ethyl acetate] to give 380 mg of the captioned difluoro ester (4).

$^1$H=NMR δ(ppm):
0.65 (3H, s), 1.05 (3H, s), 1.96 (3H, s),
1.98 (3H, s), 3.79 (3H, s), 4.85 (1H, m),
4.98 (1H, m), 5.44 (1H, m).
EI-MS (30eV) m/z:
432 (M$^+$, 62.0%), 417 (11.2), 373 (1.2),
313 (13.1), 253 (4.0), 211 (8.1), 135
(20.8), 135 (15.8), 118 (base peak).

(d) Synthesis of 1α,3β-diacetoxy-24a,24a-difluoro-24-homochlolest-5-en-25-ol (5)

A mixture of 72 mg (0.13 mmol) of the methyl 1α,3β-diacetoxy-24a,24a-difluoro-24-homochol-5-ene-25-carboxylate (4), 1.3 ml of a 1 mole THF solution of methylmagnesium bromide, and 2.5 ml of THF was stirred at room temperature for 80 minutes in an argon atmosphere. The reaction mixture was treated in a customary manner (extracted with ethyl acetate). The residue was dissolved in 1 ml of pyridine, and 1 ml of acetic anhydride was added. The mixture was stirred at room temperature for 16 hours, and treated in a customary manner (extracted with ethyl acetate). The crude product was purified by silica gel column chromatography (14 g; eluted with hexane/ethyl acetate) to give 43 mg of the captioned alcohol (5).

$^1$H=NMR δ(ppm):
0.65 (3H, s), 1.05 (3H, s), 1.30 (6H, s),
1.97 (3H, s), 1.99 (3H, s), 4.91 (1H, m),
5.08 (1H, m), 5.46 (1H, m).
EI-MS (30eV) m/z:
432 (M$^+$, 52.0%), 417 (10.8), 374 (4,3),
313 (13.3), 253 (5.4), 211 (7.8), 135
(22.3), 118 (base peak), 59 (4.9).

(e) Synthesis of 1α,3β,25-trihydroxy-24a,24a-difluoro-24-homocholesta-5,7-diene (6)

A mixture of 16 mg (0.03 mmol) of 1α,3β-diacetoxy-24a,24a-difluoro-24-homocholest-5-ene-25-ol (5) and 7.2 mg (0.04 mmol) of N-bromosuccinimide was heated under reflux in 4 ml of carbon tetrachloride for 20 minutes in an argon atmosphere. The reaction mixture was cooled to 0° C., and the precipitate formed was separated by filtration, and the solvent in the filtrate was distilled off. The resulting residue was dissolved in 4 ml of THF, and a catalytic amount of tetra-n-butyl ammonium bromide was added. While the light was shut off in an argon atmosphere, the mixture was stirred for 50 minutes. Then, 0.1 ml (0.1 mmol) of a 1 mole THF solution of tetra-n-butylammonium fluoride was added. Under the same conditions, the mixture was stirred for 30 minutes. The reaction mixture was treated in a customary manner (extracted with ethyl acetate). The crude product was dissolved in 2 ml of THF, and 1 ml of a 5% methanol solution of potassium hydroxide was added. The mixture was stirred at room temperature in an argon atmosphere for 14 hours while shutting off the light. The reaction mixture was reacted in a customary manner (extracted with ethyl acetate). The resulting crude product was purified by preparative thinlayer chromatography (developing solvent: benzene/ethyl acetate=1:1, developed four times) to give 3.1 mg of the captioned 5,7-diene (6).

UV $\lambda^{EtOH}_{max}$: 294, 282, 271 nm.

(f) Synthesis of
1α,25-dihydroxy-24a,24a-difluoro-24-homovitamin D₃
(I)

3.1 mg of 13,38,25-trihydroxy-24a,24a-difluoro-24-homocholesta-5,7-diene (6) was dissolved in a mixed solvent of 90 ml of benzene and 40 ml of ethyl acetate. The solution was exposed to ultraviolet irradiation by using a high-pressure mercury lamp (Hanovia, 200W) at 0° C. for 3 minutes in an atmosphere of argon. Subsequently, the reaction mixture was heated under reflux for 1 hour in an atmosphere of argon. The solvent was evaporated under reduced pressure. The resulting crude product was purified by preparative thin-layer silica gel column chromatography (developing solvent: benzene/ethyl acetate=1:1, developed three times) to give 421 μg of the captioned vitamin D₃ derivative (I).

UV $\lambda^{EtOH}_{max}$: 265 nm.
UV $\lambda^{EtOH}_{min}$: 228 nm.
EI-MS (70eV) m/z:
466 (M+, 15.1%), 448 (76.6), 430 (79.6),
415 (14.9), 407 (5.7), 287 (7.0), 269
(12.8), 251 (31.5). 236 (16.6), 152 (27.2),
141 (43.0), 135 (73.4), 116 (15.7), 59
(95.5), 43 (base peak), 41 (54.2).

INDUSTRIAL UTILIZABILITY

The 1α,25-dihydroxy-24a,24a-difluoro-24-homovitamin D₃ in accordance with this invention has strong vitamin D activity and low toxicity, and is useful as a drug for preventing and treating calcium pathobolism, osteoporosis, etc.

I claim:
1. 1α,25-Dihydroxy-24a,24a-difluoro-24-homovitamin D₃ represented by the following formula:

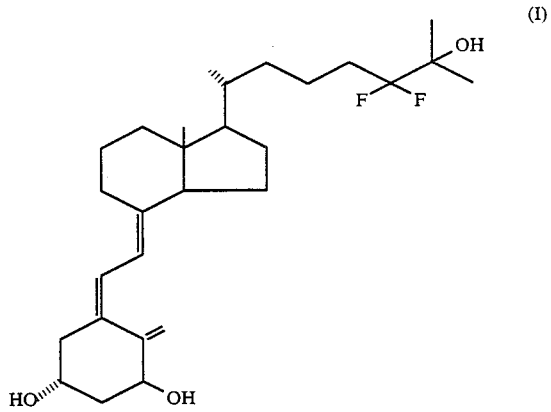

* * * * *